United States Patent [19]
Robinson et al.

[11] Patent Number: 5,258,038
[45] Date of Patent: Nov. 2, 1993

[54] PROSTHETIC FOOT WITH ANKLE JOINT AND TOE MEMBER

[75] Inventors: Eric Robinson, Madison Heights; David Robinson, Mt. Clemens, both of Mich.

[73] Assignee: College Park Industries, Inc., Southfield, Mich.

[21] Appl. No.: 698,557

[22] Filed: May 10, 1991

[51] Int. Cl.5 .............................................. A61F 2/66
[52] U.S. Cl. ...................................... 623/49; 623/52; 623/55; 623/47
[58] Field of Search .................................... 623/47-56

[56] References Cited

U.S. PATENT DOCUMENTS

| | | | |
|---|---|---|---|
| 2,197,093 | 4/1940 | Campbell | 623/56 |
| 2,215,525 | 9/1940 | Jeter | 623/49 |
| 2,475,372 | 7/1949 | Catranis | 623/54 X |
| 2,475,373 | 7/1949 | Catranis . |  |
| 2,644,165 | 7/1953 | Grisoni . |  |
| 2,731,645 | 1/1956 | Woodall . |  |
| 2,863,684 | 12/1958 | Carroll | 623/47 |
| 3,551,914 | 1/1971 | Woodall . |  |
| 4,007,497 | 2/1977 | Haupt . |  |
| 4,360,931 | 11/1982 | Hampton | 623/55 X |
| 4,645,509 | 2/1987 | Poggi et al. | 623/55 |
| 4,892,554 | 1/1990 | Robinson | 623/55 |

FOREIGN PATENT DOCUMENTS

| | | | |
|---|---|---|---|
| 922990 | 6/1947 | France | 623/53 |
| 526356 | 9/1976 | U.S.S.R. | 623/53 |
| 1454450 | 1/1989 | U.S.S.R. | 623/55 |
| 1498490 | 8/1989 | U.S.S.R. | 623/53 |
| 518258 | 2/1940 | United Kingdom | 623/53 |

OTHER PUBLICATIONS

Flex Foot advertising material.
The Quantum Advertising Material (1988).
Flex Foot Split Toe Option.

*Primary Examiner*—Randall L. Green
*Assistant Examiner*—D. Willse
*Attorney, Agent, or Firm*—Steven L. Permut

[57] ABSTRACT

A prosthetic foot includes an ankle member, a heel member and a toe member coupled to each other for relative pivotable movement with the pivotable movement resisted by elastomeric pads. The heel and ankle member are connected through a joint allowing for translational and pivotable torsional motion of the ankle with respect to the heel and provided with limit stops in the axle and the side walls of the heel member to limit the torsional and translation motion of the ankle joint. The toe member is formed symmetrically to be used for left and right feet with symmetrically positioned and mirror imaged fore sections.

18 Claims, 4 Drawing Sheets

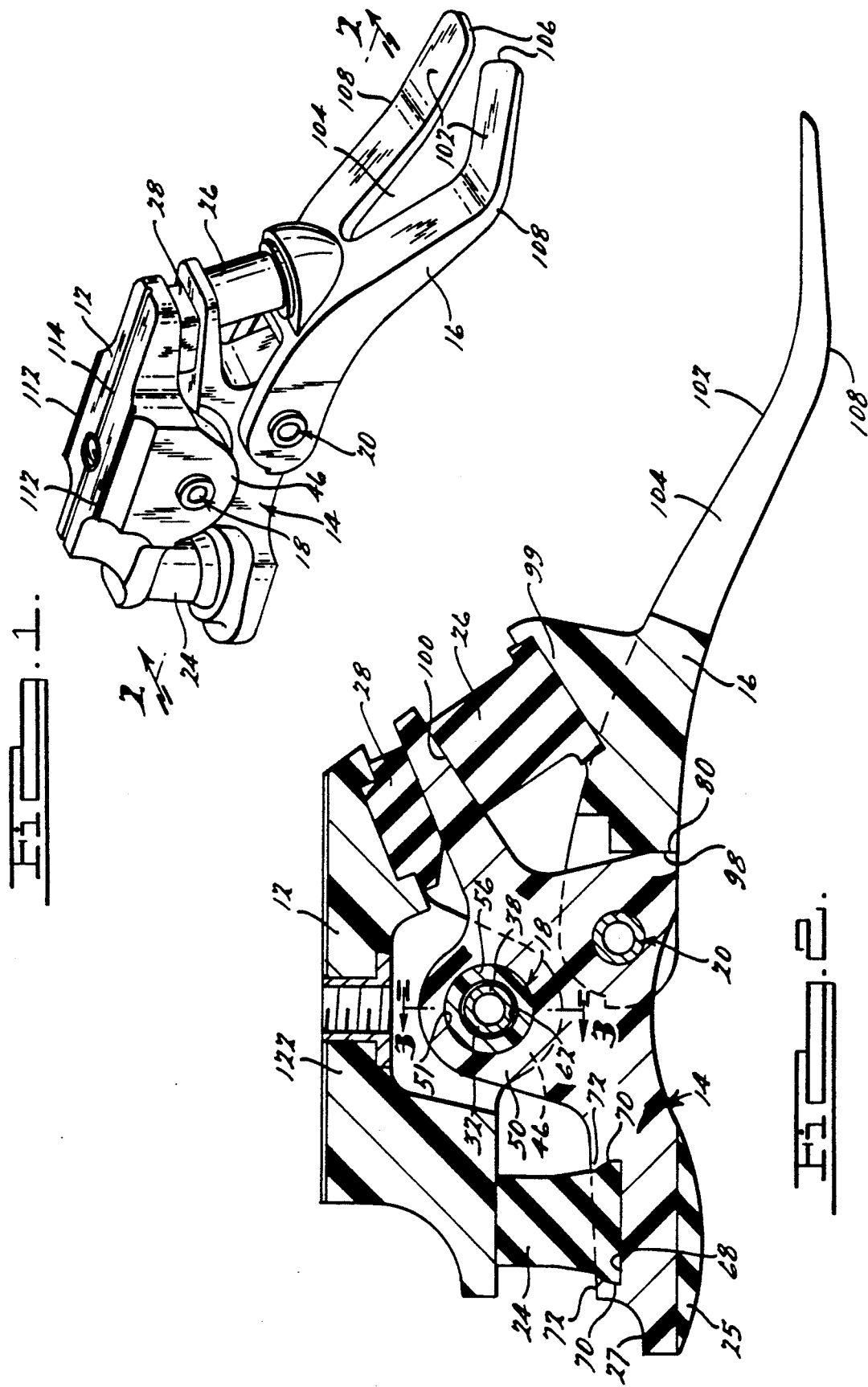

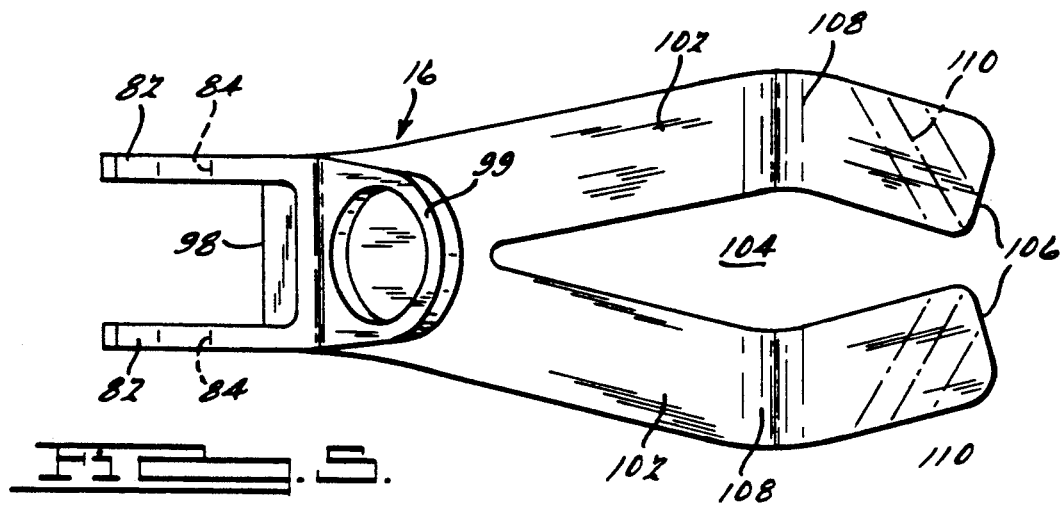
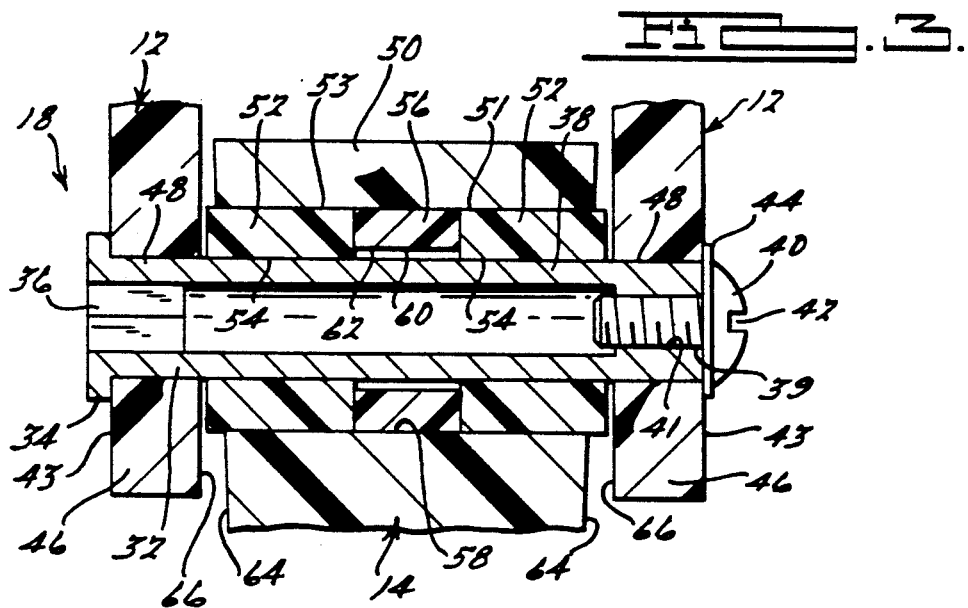
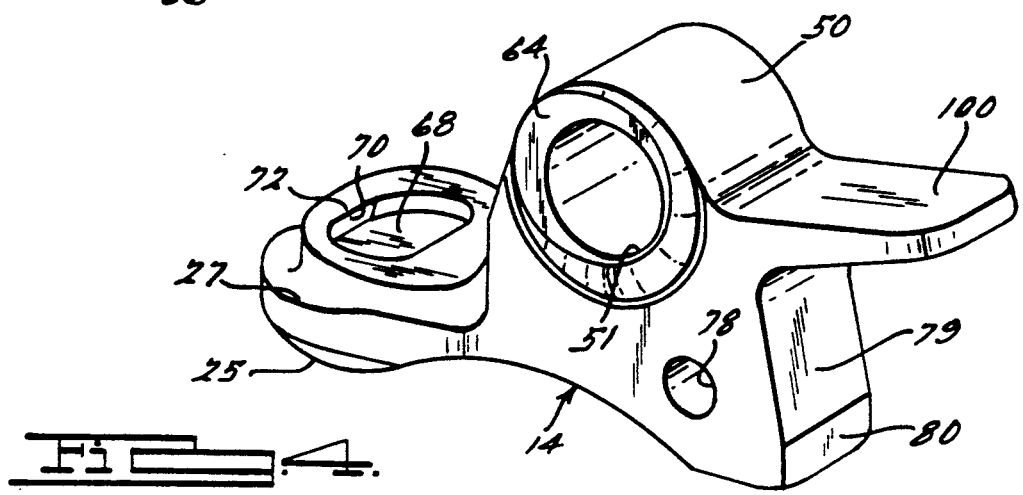

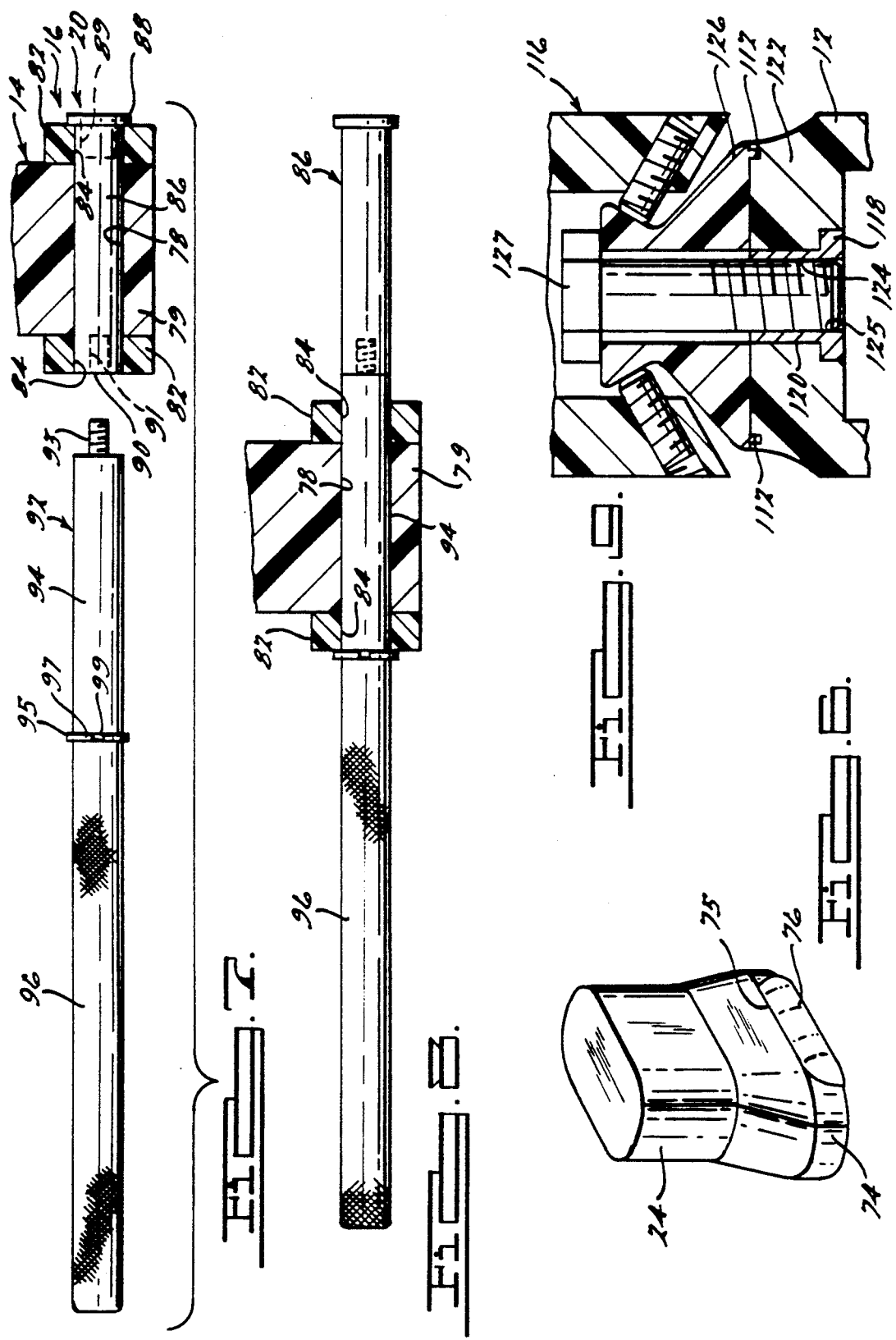

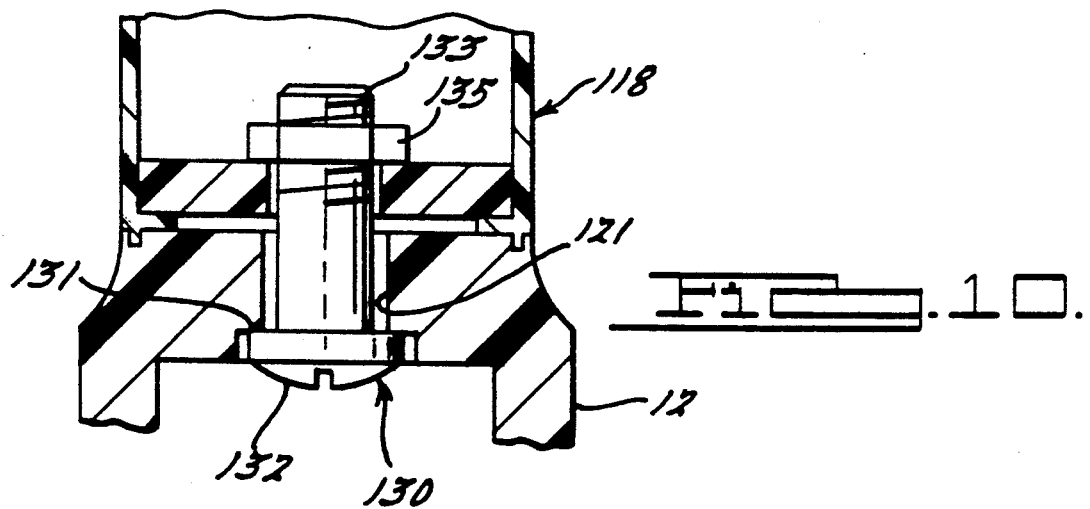

PROSTHETIC FOOT WITH ANKLE JOINT AND TOE MEMBER

TECHNICAL FIELD

This invention relates to prosthetic feet and more particularly to a multi-piece prosthetic foot having an ankle member, heel member and toe member.

BACKGROUND OF THE INVENTION

The basic requirements of an acceptable prosthetic foot are that it will provide a stable support for the amputee throughout a reasonable range of activities and permit the amputee to walk with a normal stride. To achieve this normal stride, the prosthetic foot must flex during walking as the foot continually moves through the heel-strike, foot-flat and toe-off cycle. It must also throughout this cycle, provide transverse stability particularly at the toe-off, when the entire weight of the amputee is applied to the forward portion of the prosthetic foot. Prior art prosthetic feet typically are substantially transversely inflexible, which interferes with side to side balancing when walking on uneven surfaces. Unlike natural foot, the prosthetic foot does not sense or correct itself with this unevenness and an unanticipated sideways tilting of the foot at toe-off results in an imbalance at a critical portion of the stride.

Amputees are no longer satisfied to sit in a wheel chair or be content with a stilted walking motion. An amputee often strives to duplicate physical activities which were conducted before the amputation. These activities may include rigorous physical activities such as running, playing basketball and dancing.

Prosthetic feet to be commercially acceptable must duplicate the motions of the natural foot as much as possible. These motions include side to side stability at the toe section of the foot where weight can be exerted on each side of the foot. The ankle joint must have torsional flexibility transverse to the up and down motion of the ankle which pivotably lowers and raises the foot.

The added torsional motion of the joint in the artificial foot adds a degree of stress on the resilient pads between the members of the artificial foot not otherwise present in a foot that has limited motion in only the up and down direction relative to pivotable raising and lowering of the foot.

The torsional flexing must be limited and must be direction sensitive to provide a more lifelike ankle action. Secondly the resilient pad between the members of the feet must be positively anchored to resist being displaced during torsional motion of the ankle joint.

It is further required to have a commercially viable foot that has a formed symmetrical toe member that is used for both left and right feet so that inventory is reduced. The toe member must be shearable to conform to the contour of smaller sized left or right feet.

SUMMARY OF THE INVENTION

In accordance with one aspect of the invention, a prosthetic foot has an ankle member pivotally connected to a heel member which is in turn pivotally connected to a toe member about two substantially parallel axles. The toe member is symmetrically formed with a elongated slot starting at the forward end of the toe member bifurcating the toe section into two symmetrically positioned and mirror imaged toe sections.

In accordance with another aspect of the invention, the ankle axle passes through two spaced resilient bushings that are positioned in an aperture transversely extending through the heel member. The ankle member has two shoulder sections with apertures therethrough that are aligned with the aperture through the heel member to form a passage for the axle. Interposed between the two elastomeric bushings is a semi-rigid bearing with an outer diameter sized to be snugly and slidably received in the central aperture of the heel. The bearing has an inner diameter sized slightly larger than the outer diameter of the axle to provide for limited transverse motion of the axle within the aperture. The inner diameter provides for an axle stop after a predetermined amount of resilient deformation of the bushings.

In accordance with another aspect of the invention, the ankle joint includes one of the heel and ankle members having a stop limit. The stop limit includes first and second oppositely canted abutment surfaces circumferentially positioned about the passage receiving the axle and constructed to abut complementary abutments on the other of the heel and ankle member to limit pivotable motion transverse to the longitudinal axis of the axle. In one embodiment, the canted abutments are annular flat shoulders canted with respect to the longitudinal axis of the axle. Transverse pivotable motion about the central axis along the first direction is provided for a first predetermined amount and transverse pivotable motion about a second direction is provided for a second different predetermined amount before the abutments stop the pivotable motion.

According to another aspect of the invention, the axles connecting the heel member to one of the toe members and ankle member includes a pin with an integral stop shoulder for engagement to a side of the foot. One end of the axle has a recessed tool engaging mechanism for non-rotatably engaging a tool at said one end. The opposite end of the axle pin has a fastener engaging section for connection to a fastener. The fastener has a stop shoulder for engagement to another side of the foot about the end of the passage. The fastener has a tool engaging mechanism wherein the axle can be tightened such that the stop shoulders snugly abut against the sides of the foot.

In accordance with another aspect of the invention, an assembly tool has a axle engaging section for engaging the fastener receiving section of the axle pin and a cylindrical section for insertion into the apertures of the respective toe, heel and ankle members and a handle section for gripping the tool. A stop shoulder is interposed between the handle section and cylindrical section for providing a stop against a side of the foot for when the tool is inserted into the apertures and when the pin has fully been extended out of the apertures.

In accordance with another aspect of the invention, the ankle member is adaptable to be mounted to either an endoskeletal leg member or exoskeletal leg member. The ankle member has a threaded passageway therethrough which receives a threaded fitting. A threaded fitting has an oppositely threaded interior aperture which engages a downwardly extending fastener from an endoskeleton. Removal of the insert allows for an upwardly extending fastener to pass through the aperture to engage an exoskeleton.

According to another aspect of the invention, at least one of the resilient bumpers interposed between two of the foot members is positively anchored in place by means of a recess in one of the foot members having a lip extending over the recess which positively engages the resilient elastomeric pad. Preferably, the resilient elastomeric pad has a ear extending at one end which extends into the recess.

In this fashion, a foot having fewer number of inventory parts can be assembled to accommodate high heels and other shoes of different heel heights and provide a torsionally resilient ankle that allows torsional flexing of the foot within limits that are dependent on the relative pivotal position of the heel with respect to the ankle member about the ankle joint. Furthermore the bifurcated toe provides for side to side stability. The symmetrical shape of the formed toe member allows for one toe member to be used for either left or right prosthetic feet. One of the toe members can be cut to allow for conformation of the small toe side to accommodate smaller sized shoes and feet sizes. In addition, positively anchored elastomeric members are maintained in position in the foot to provide for a stable member against torsional motion of one foot member with respect to another.

BRIEF DESCRIPTION OF THE DRAWINGS

Reference now is made to the accompanying drawings in which:

FIG. 1 is a perspective view of a prosthetic foot skeletal structure embodying the present invention;

FIG. 2 is a cross sectional view taken along the lines 2—2 in FIG. 1;

FIG. 3 is a fragmentary cross sectional view taken along the lines 3—3 shown in FIG. 2;

FIG. 4 is a perspective view of the heel member shown in FIG. 1;

FIG. 5 is a top plan view of the toe member shown in FIG. 1;

FIG. 6 is a perspective view of the rear elastomeric pad shown in FIG. 1;

FIG. 7 is a view of the heel toe axle connection partially dissembled for engagement to an assembly and disassembly tool;

FIG. 8 is a view similar to FIG. 7 showing the tool pushing out the axle for disassembly;

FIG. 9 is a view showing the ankle member mounted to an endoskeleton leg portion; and FIG. 10 is a fragmentary view showing the ankle member mounted to an exoskeleton leg portion;

DETAILED DESCRIPTION OF THE PREFERRED EMBODIMENTS

Referring to FIGS. 1 and 2, a prosthetic foot 10 has an ankle member 12, a heel member 14 and toe member 16. The ankle member 12 is pivotably connected to heel member 14 through an axle joint 18. The heel member 14 is pivotably connected to toe member 16 through axle joint 20. The heel, ankle and toe members are made from a suitable synthetic thermoplastic or composite material such as graphite that can be fiberglass-reinforced. The axle joints 18 and 20 provide for pivotable motion of the three members along the axis of the axle joints which runs transverse to the longitudinal axis of the foot; i.e., the length of the foot. Furthermore as explained below, the axle joint 18 provides for limited torsional or pivotable motion about a direction transverse to the longitudinal axis of the axle 18.

Elastomeric pad 24 provides for resilient resistance of heel member with respect to ankle member 12 against clockwise motion as referenced in FIG. 2. Elastomeric pad 26 resists upward counterclockwise motion of toe member 16 with respect to the heel member 14 and elastomeric pad 28 resists clockwise motion of the heel member with respect to the ankle member. The pads 24, 26, 28 can be selected by size and durometer to accommodate different people's weight, size and personal preferences. A heel pad 25 is bonded to the rear lower section 27 to also absorb shock and vibration. As shown in phantom in FIG. 11 when assembled, the elastomeric pads and foot members 12, 14 and 16 can be covered by a firm resilient elastomeric outer layer 30 whose outer surface is cosmetically conformed to that of a natural foot.

Referring now to FIGS. 2 and 3 the axle joint 18 includes an axle or pin 32 which has one end having an abutment shoulder 34 sized to abut one side 43 of the member 12. The end 35 has a cavity 36 therein which is conformed to non-rotatable receive a tool such as an allen wrench. The pin 32 has a cylindrical section 38 and a second end 39 with an internally threaded section 41 axially positioned within cylindrical section 38. Section 41 receives a threaded fastener 40. The fastener 40 also has a tool receiving cavity or recess 42 therein that can receive an allen wrench or a screwdriver. The fastener 40 may include a washer 44 sized to abut another side 43 of ankle member 12.

The ankle member 12 has two flange sections 46, each with an aperture 48 that receives the pin 32. The flanges 46 are spaced apart to receive the central section 50 of heel member 14. The central section 50 has an aperture 51 which is significantly larger than the outer diameter of pin cylindrical section 38. Two rubber or resilient elastomeric bushings 52 have an outer diameter 53 sized to be snugly received in aperture 51 and have an inner diameter 54 sized to snugly receive the cylindrical portion 38 of pin 32. Axially interposed between the bushings 52 is a semi-rigid plastic bushing 56 made from Delrin having an outer diameter 58 sized to be slidably snugly received in aperture 51 and an inner diameter 60 which is sized larger than the outer diameter of cylindrical section 38 to provide for an annular gap 62 therebetween. The mounting section 50 has tapered sidewalls 64 which are oppositely angled with respect to each other on opposite sides of aperture 50 and are slightly spaced from inner walls 66 of flanges 46.

The bushings 52 provide for both translational motion of the ankle member with respect to the heel member and torsional or pivotal motion which is transverse to the longitudinal axis of pin 32 when in the rest position. However the translational motion is limited by the inner diameter 60 of bushing 56 such that upon translational motion of a predetermined amount, the pin cylindrical section 38 abuts the internal diameter 60 of the bushing 56 which resists further translational motion. Pivoting motion of the pin 32 is limited by the tapered shoulder 64 abutting the interior walls 66 of flanges 46. Because the walls 64 are tapered in a direction as shown in FIG. 4, when the ankle is pivoted either clockwise or counterclockwise from the position shown in FIG. 2, the amount of torsional pivoting between the ankle and heel member will differ. In other words different amounts of torsional motion may be allowed at different relative positions of the ankle member with respect to the heel member. Less torsional flexibility may be provided when the elastomeric bumper 24 is significantly compressed such that the heel is rotated clockwise with respect to the ankle member 12. This different torsional motion dependent upon the position of the ankle more realistically imitates a natural ankle at its varying elevated positions.

Because torsional motion may exert a sideways pulling force on elastomeric pad 24, elastomeric pad 24 needs to be positively engaged within the heel member. This is accomplished by a cavity 68 having a recess 70. The heel member has a lip 72 extending over the recess 70 to positively engage the elastomeric pad 24. As shown in FIG. 6, the elastomeric pad 24 has a substantially oval lower section 74 with a substantially longer side 75 of the oval section having a protruding ear 76 which can be received in recess 70.

Referring now to FIGS. 4, 5, 7 and 8, the axle joint 20 between the heel member 14 and toe member 16 provides pivoting motion of the toe in an up and down direction. The heel member 14 has a central aperture 78 at a lower section in proximity to an abutment shoulder 80. The toe member has two flanges 82 with apertures 84 therethrough that are aligned with respect to each other. The flanges 82 are spaced apart to receive the lower section 79 of heel member 14. The aperture 78 and 80 are aligned to snugly and slidably receive a pin 86 that is similarly constructed to pin 32 with a flange end 88 having a recess 89 adapted to non-rotatably receive a tool such as an allen wrench. A second end 90 has a threaded cavity 91 adapted to receive either a fastener 40 or a tool 92 as shown in FIGS. 7 and 8. The tool 92 has a threaded section 93 engagable to threaded section 91 of cylindrical section 94 and hand gripping section 96. A stop shoulder 95 is interposed between the hand gripping section 96 and cylindrical section 94. The stop shoulder 95 can be integral or be a separate clip member 97 engaged in a groove 99. Cylindrical section 94 has an outer diameter equal to the outer diameter of pin 86 that passes through apertures 84 and 78. The assembly of either axle 18 or 20 is expedited with the use of tool 92.

The tool as shown in FIG. 7 can be engaged with the threaded section 91. The tool is pushed by force exerted on handle section 96 to slide the pin outwardly. The section 92 passes through the apertures 84 and 78 until the stop shoulder 95 abuts the flange 82 as shown in FIG. 8. At this time the pin 86 can be unthreaded from section 93. The hand grip then is pulled back such that section 94 is withdrawn from the apertures 84 and 78 to disassemble the axle joint 18. Assembly of the axle joint 18 is achieved by reversing the steps. The pin tool 92 is inserted into the axle apertures. The pin 86 is then threaded onto the section 93 and the handle section 96 is pulled thereby pulling the pin 92 into the apertures. Fastener 40 is then threaded onto pin 32.

A similar process is also used for axle joint 20. The toe section between flanges 82 has an abutment shoulder 98 which abuts the abutment shoulder 80 of heel member 14 to provide for a limit stop in the downward motion of toe member 16 relative to the heel member 14. The toe member has a mounting section 99 which receives elastomeric pad 26 which abuts flange section 100 of heel member 14. The elastomeric pad 26 provides resilient resistance against the upward pivotal motion of toe member 16 relative to the heel member 14. The toe member 16 has two symmetrically positioned and mirror imaged toes 102 with a bifurcating slot 104 therebetween which extends from the front distal ends 106 of toes 102. Each toe has a ball support section 108 which supports weight at the rest position.

As shown in FIG. 5, the symmetry of the toe members 102 allows for one toe member 16 to be manufactured for both left and right feet. If a particular foot size is small, for contour purposes the outer or small toes need to be shortened. This contour can be easily accomplished by cutting one of the toe members 102 for example along one of the dotted lines 110 to provide for a shorter outer toe which would fit within a smaller cosmetic outer foot cover and a smaller sized shoe. However for standard and larger feet, the toes 102 need no trimming. The ball or weight bearing sections 108 are independently flexible such that one toe member 102 can be flexed and change its height relative to the vertical position of the other toe member. Each toe section 102 diverges from the axle joint 20 to the weight supporting section 108 of each toe section. Furthermore, each toe section 102 converges toward each other from weight supporting section 108 to distal end 106.

The ankle member is adaptable to be attached to either an endoskeleton as shown in FIG. 9 or an exoskeleton as shown in FIG. 10. The ankle member has longitudinal slots 112 and 114 which non-rotatably engage standard attachments such as Otto Bock endoskeletal and exoskeletal systems and/or adapters. The endoskeletal and exoskeletal systems as shown in FIGS. 9 and 10 are standard and form no part of the invention. The ankle member 12, however, is adaptable to be connected to either system. The ankle section member 14 can be connected to an exoskeletal connection 118 as shown in FIG. 10. A bolt 130 having an enlarged head 132 passes upward through the aperture 121 with the bolt head engaging the recessed flange 131 of ankle member 14. The threaded portion 133 of the bolt then engages the endoskeleton fastener 135.

For attachment to an endoskeleton as shown in FIG. 9, a top portion 122 of the ankle 12 has the aperture 120 resized. Threaded insert 118 self taps in aperture 120. The threaded insert 118 has an interior opposite threaded aperture 124. A bolt 127 extends through the endoskeletal adaptor 126 and threadably engages threaded aperture 124.

Variations and modifications of the present invention are possible without departing from its scope and spirit as defined by the appended claims.

The embodiments of the invention in which an exclusive property or privilege is claimed are defined as follows:

1. In an artificial foot having an ankle member, a heel member, and a toe region, said heel member pivotably connected to said ankle member and about a first transverse axle; said improvement comprising:
   one of said heel and ankle members having one central aperture transversely passing therethrough;
   the other of said heel and ankle members having two shoulder sections with an aperture through each shoulder section aligned with each other;
   said one member positionable between said shoulders of said other member;
   said central aperture having a diameter larger than the diameter of said first axle;
   said central aperture having a pair of resilient bushings positioned within said central aperture near respective ends thereof, each bushing having an inner diameter sized to snugly receive said first axle;
   a stop limiter positioned between said resilient bushings for limiting motion of said axle transverse to its longitudinal axis.

2. In an artificial foot as defined in claim 1 further comprising:

said limiter being a semi-rigid bushing fitted in said central aperture having an outer diameter substantially equal to the diameter of said aperture and an inner diameter slightly larger than said diameter of said first axle.

3. In an artificial foot as defined in claim 2 further comprising:

said member with said central aperture having tapered shoulders to provide a predetermined limit of pivotable motion along a first direction and a second predetermined limit of pivotable motion along a second direction between said heel and ankle members with said pivotable motion being transverse to said longitudinal axis of said first axle.

4. In an artificial foot as defined in claim 1 further comprising:

a tool having an axle engaging section engagable to a fastener engaging section of a pin of said axle;

said tool having a cylindrical section insertable in a passage defined by said central aperture and said apertures in said shoulder sections to push said first axle out of said passage and pull said first axle into said passage;

said tool having a hand engaging section for an operator to manually grasp said tool;

said tool having a stop shoulder positioned between said cylindrical section and said hand engaging section for abutting against said foot about one of said apertures.

5. In an artificial foot as defined in claim 1 further comprising:

said toe region having an elongate slot therethrough extending longitudinally rearwardly from a forward end of said toe region bifurcating said toe region into two symmetrically positioned and substantially mirror imaged toe sections.

6. In an artificial foot as defined in claim 5 further comprising:

each of said toe sections being constructed out of resilient biasing flexible material for providing resilient flexing of one toe section with respect to the other when a weight is exerted on a weight supporting section of one toe section.

7. In an artificial foot as defined in claim 5 further comprising:

said toe sections diverging forwardly from a pivotable connection of the toe region with the heel member to a weight bearing section at each toe section.

8. In an artificial foot as defined in claim 7 further comprising:

said toe sections converging toward each other from the weight supporting section of each toe section to a distal tip of each toe section.

9. In an artificial foot as defined in claim 1 further comprising:

a pivotable connection between said heel member and said toe region including a separate toe member for resiliently resisted pivotal movement about a second transverse axle;

said heel member and toe member each having a central abutment shoulder that abut each other to define an end limit to downward pivotable movement of a forward section of said toe member with respect to said heel member.

10. In an artificial foot as defined in claim 9 further comprising:

said toe member having an elongate slot therethrough extending longitudinally rearwardly from a forward end of said toe member bifurcating said toe member into two symmetrically positioned and substantially mirror imaged toe sections.

11. In an artificial foot as defined in claim 10 further comprising:

each of said toe section being constructed out of resilient biasing flexible material for providing resilient flexing of one toe section with respect to the other when a weight is exerted on a weight supporting section of one toe member.

12. In an artificial foot as defined in claim 10 further comprising:

said toe sections diverging forwardly from a pivotable connection of the toe member with the heel member to a weight bearing section at each toe section.

13. In an artificial foot as defined in claim 12 further comprising:

said toe sections converging toward each other from the weight supporting section of each toe section to a distal tip of each toe section.

14. In an artificial foot as defined in claim 1, further comprising:

said ankle member having an aperture therethrough at an upper section that receives a bolt for connection with an endoskeletal leg member and a threaded insert insertable in said aperture for connection to an adapter and a threaded fastener extending downward from an endoskeletal leg member through said adapter;

said ankle member and adapter being non-rotatably connected to each other.

15. In an artificial foot having an ankle member, heel member and toe member pivotably connected together, the improvement comprising:

said toe member formed with an elongated slot therethrough extending longitudinally rearwardly from a forward end of said toe member bifurcating said toe member into two symmetrically positioned and substantially mirror imaged toe sections that diverge in separate, generally anterior directions from a pivotable connection of the toe member to the heel member with a weight bearing section at each toe section.

16. In an artificial foot as defined in claim 15 further comprising:

said pivotable connection between said heel member and said toe member for resiliently resisted pivotal movement being about a second transverse axle, said heel member and toe member each having a central abutment shoulder that abut each other to define an end limit to downward pivotable movement of a forward section of said toe member with respect to said heel member.

17. In an artificial foot as defined in claim 15 further comprising:

said toe sections converging toward each other from the weight supporting section of each toe section to a distal tip of each toe section.

18. In an artificial foot as defined in claim 15 further comprising:

each of said toe sections being constructed out of resilient biasing flexible material for providing resilient flexing of one toe section with respect to the other when a weight is exerted on said weight supporting section of one toe member.

* * * * *